US008394494B2

(12) United States Patent
Ohrlander et al.

(10) Patent No.: US 8,394,494 B2
(45) Date of Patent: *Mar. 12, 2013

(54) ANTIMICROBIAL SUBSTRATES AND USES THEREOF

(75) Inventors: Mattias Ohrlander, Enskede (SE); Billy Sodervall, Markaryd (SE)

(73) Assignee: Bactiguard AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/155,334

(22) Filed: Jun. 7, 2011

(65) Prior Publication Data

US 2011/0236441 A1 Sep. 29, 2011

Related U.S. Application Data

(62) Division of application No. 11/784,558, filed on Apr. 5, 2007, now abandoned.

(60) Provisional application No. 60/790,307, filed on Apr. 7, 2006.

(51) Int. Cl.
*B32B 5/16* (2006.01)
*B05D 1/12* (2006.01)
*A61K 9/00* (2006.01)
*A61K 33/38* (2006.01)

(52) U.S. Cl. ........ 428/328; 428/451; 424/400; 424/618; 977/773

(58) Field of Classification Search .................. 428/328, 428/180, 618, 521; 424/400, 618; 977/773
See application file for complete search history.

(56) References Cited

U.S. PATENT DOCUMENTS

| | | | |
|---|---|---|---|
| 4,795,475 A | 1/1989 | Walker | |
| 5,320,908 A * | 6/1994 | Sodervall et al. | 428/461 |
| 5,395,651 A | 3/1995 | Sodervall et al. | |
| 5,695,857 A | 12/1997 | Burrell et al. | |
| 5,747,178 A | 5/1998 | Sodervall et al. | |
| 5,753,251 A | 5/1998 | Burrell et al. | |
| 5,935,719 A | 8/1999 | Abbott | |
| 5,965,204 A | 10/1999 | Sodervall et al. | |
| 6,080,490 A | 6/2000 | Burrell et al. | |
| 6,168,633 B1 | 1/2001 | Shoher et al. | |
| 6,224,983 B1 | 5/2001 | Sodervall et al. | |
| 6,284,387 B1 | 9/2001 | Nakao | |
| 6,399,039 B2 | 6/2002 | Ostgard | |
| 6,716,895 B1 | 4/2004 | Terry | |
| 6,831,024 B2 | 12/2004 | Kim | |
| 7,195,615 B2 | 3/2007 | Tan | |
| 2004/0121077 A1 | 6/2004 | Park et al. | |
| 2005/0159306 A1 | 7/2005 | Kezuka et al. | |
| 2006/0003019 A1 | 1/2006 | Moller et al. | |
| 2006/0251874 A1 | 11/2006 | McClure et al. | |
| 2007/0237945 A1 | 10/2007 | Ohrlander et al. | |
| 2007/0237946 A1 | 10/2007 | Ohrlander et al. | |

FOREIGN PATENT DOCUMENTS

| | | |
|---|---|---|
| CA | 2016081 C | 4/1999 |
| CH | 654738 A5 * | 3/1986 |
| EP | 0400349 A1 | 12/1990 |
| EP | 0693576 A1 | 1/1996 |
| EP | 0937398 A1 | 8/1999 |
| EP | 1375700 A1 | 1/2004 |
| JP | 63-200752 A | 8/1988 |
| JP | 11-302570 A | 11/1999 |
| JP | 2001-234392 A | 8/2001 |
| WO | 02/17984 A1 | 3/2002 |
| WO | 03/063925 A1 | 8/2003 |
| WO | 03/076341 A2 | 9/2003 |
| WO | 2004/045577 A1 | 6/2004 |
| WO | 2005/072281 A2 | 8/2005 |
| WO | 2005/073289 A1 | 8/2005 |
| WO | WO 2005073289 A1 * | 8/2005 |
| WO | 2005/072281 A3 | 11/2005 |

OTHER PUBLICATIONS

Final Office Action received for U.S. Appl. No. 11/784,332, mailed on Jul. 27, 2011, 12 pages.
Non Final Office Action received for U.S. Appl. No. 11/784,332, mailed on Jan. 24, 2012, 7 pages.
Final Office Action received for U.S. Appl. No. 12/296,429, mailed on Mar. 9, 2012, 15 pages.
International Search Report received for PCT Patent Application No. PCT/SE2006/050485, mailed on Mar. 1, 2007, 5 pages.
International Search Report received for PCT Patent Application No. PCT/SE2007/050226, mailed on Jul. 4, 2007, 6 pages.
International Search Report received for PCT Patent Application No. PCT/SE2007/050225, mailed on Jul. 4, 2007, 6 pages.
Moller et al., "A New Approach for Biologically-Inhibiting Surfaces", Journal of Applied Surface Finishing, vol. 2, No. 2, 2007, pp. 149-157.
Saygan et al., "Gold and Gold-Palladium Coated Polypropylene Grafts in a *S. epidermidis* Wound Infection Model", Journal of Surgical Research, vol. 131, 2006, pp. 73-79.
U.S. Appl. No. 07/347,016, filed May 4, 1989 for Sodervall et al.
U.S. Appl. No. 07/630,333, filed Dec. 13, 1990, for Sodervall et al.
Gabriel et al., "Effects of Silver on Adherence of Bacteria to Urinary Catheters: In Vitro Studies", Current Microbiology, vol. 30, 1995, pp. 17-22.
Non Final Office Action received for U.S. Appl. No. 11/784,332, mailed on Feb. 19, 2010, 22 pages.

(Continued)

*Primary Examiner* — Michael M Bernshteyn
(74) *Attorney, Agent, or Firm* — Morrison & Foerster LLP

(57) ABSTRACT

A new substrate makes it possible to modify surface properties relating to antimicrobial properties. Said substrate has an electron donating surface, characterized in having metal particles on said surface, said metal particles comprising palladium and at least one metal chosen from gold, ruthenium, rhodium, osmium, iridium, and platinum, wherein the amount of said metal particles is from about 0.001 to about 8 μg/cm². The substrate is suggested for different uses, such as for modifying the hydrophobicity, protein adsorption, adhesion of bacteria, as well as preventing bacterial transmission and in particular preventing nosocomial infections.

18 Claims, No Drawings

OTHER PUBLICATIONS

U.S. Appl. No. 12/296,429, filed Apr. 5, 2007 for Ohrlander et al.
Non Final Office Action received for U.S. Appl. No. 11/784,558, mailed on Mar. 24, 2010, 18 pages.
Non Final Office Action received for U.S. Appl. No. 11/784,332, mailed on Aug. 4, 2010, 12 pages.
Final Office Action received for U.S. Appl. No. 11/784,558, mailed on Dec. 8, 2010, 17 Pages.
Non Final Office Action received for U.S. Appl. No. 11/784,332, mailed on Dec. 23, 2010, 12 pages.
Non Final Office Action received for U.S. Appl. No. 12/296,429, mailed on Jul. 12, 2011, 25 pages.

* cited by examiner

ANTIMICROBIAL SUBSTRATES AND USES THEREOF

CROSS REFERENCE TO RELATED APPLICATIONS

This application is a Divisional application of U.S. patent application Ser. No. 11/784,558, with a filing date of Apr. 5, 2007, which claims priority to U.S. Patent Provisional Application Ser. No. 60/790,307, with a filing date of Apr. 7, 2006, all of which are hereby incorporated by reference in the present disclosure in their entirety.

FIELD OF THE INVENTION

The present invention relates to a new antimicrobial substrate with nano particles, which makes it possible to modify surface properties relating to antimicrobial properties in a repeatable and controlled manner. Examples of surface properties, which can be modified, include but are not limited to hydrophobicity, protein adsorption, and adhesion of bacteria. Examples of uses of the present substrate include but are not limited to delaying colonisation of bacteria, preventing transmission of bacteria and in particular nosocomial infections. The present invention further relates to objects comprising said new substrate. The present invention further relates to the use of said substrate. Finally the present invention relates to a method for the manufacture of such a substrate.

BACKGROUND

It has always been desirable to modify surface characteristics to achieve useful properties. In particular it is desired to be able to modify surface properties that are important in connection with antimicrobial objects.

SHORT SUMMARY OF THE PRESENT INVENTION

A problem in the state of the art regarding surfaces is how to provide a surface which for example is antimicrobial, wherein it in a repeatable way is possible to modify the hydrophobicity, protein adsorption, and adhesion of bacteria.

The present inventors have discovered that the above-mentioned problem in the state of the art is solved by a substrate having an electron donating surface, characterized in that there are metal particles on the surface. The metal particles include palladium and at least one metal chosen from gold, ruthenium, rhodium, osmium, iridium, and platinum and wherein the amount of said metal particles is from about 0.001 to about 8 µg/cm$^2$. Further embodiments of the present invention are defined in the appended dependent claims.

DESCRIPTION

Definitions

Before the invention is disclosed and described in detail, it is to be understood that this invention is not limited to particular configurations, process steps and materials disclosed herein as such configurations, process steps and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

The following terms are used throughout the description and the claims.

"Adhesion of bacteria" as used herein describes the phenomenon where bacteria adhere to a surface.

"Antimicrobial" as used herein encompasses the property of suppressing and/or eliminating microbial growth.

"Colonisation" as used herein encompasses the establishment of colonies of for instance bacteria.

"Contact angle". For a given droplet on a solid surface the contact angle is a measurement of the angle formed between the surface of a solid and the line tangent to the droplet radius from the point of contact with the solid.

"Electron donating material" as used herein encompasses a material, which in connection with another more noble material has the ability to transfer electrons to the more noble material. An example is a less noble metal together with a more noble metal.

"Electron donating surface" as used herein encompasses a surface layer comprising an electron donating material.

"Hydrophobicity" of a surface as used herein describes the interactions between the surface and water. Hydrophobic surfaces have little or no tendency to adsorb water and water tends to "bead" on their surfaces. The term hydrophobicity of a surface is also closely linked with its surface energy. Whereas surface energy describes interactions of the surface with all molecules, the hydrophobicity describes the interactions of the surface with water.

"Hysteresis of contact angle" as used herein is the difference between the advancing and receding contact angle values. The advancing contact angle of a drop of water on a surface is the contact angle when the boundary between water and air is moving over and wetting the surface, while the receding angle is the contact angle when boundary between water and air is withdrawn over a pre-wetted surface.

"Modify" either means reducing or enhancing a property.

"Noble" is used herein in a relative sense. It is used to relate materials including metals to each other depending on how they interact with each other. When two metals are submerged in an electrolyte, while electrically connected, the term "less noble" metal is used to denote the metal which experiences galvanic corrosion. The term "more noble" is used to denote the other metal. Electrons will be transferred from the "less noble" metal to the more noble metal.

"Nosocomial infection" as used herein describes an infectious disease spreading for instance in a hospital environment.

"Protein adsorption" as used herein encompasses the phenomenon where proteins adhere to a surface due to overall attractive forces between the proteins and the surface.

"Substrate" as used herein is the base, which includes the material that is treated according to the present invention.

DETAILED DESCRIPTION OF THE PRESENT INVENTION

According to the present invention a substrate is treated to give it desired properties. The substrate can be made of a wide range of materials. In one embodiment the substrate is made of a material, which has an electron-donating surface. In the case of an electron-donating surface the metal particles can be applied directly on to the electron-donating surface. In the case where the surface it not electron donating, a layer of an electron donating material has to be applied to create an electron donating surface.

The present disclosure describes a substrate having an electron donating surface. The substrate includes metal particles on said surface. The metal particles include palladium and at least one metal chosen from gold, ruthenium, rhodium, osmium, iridium, and platinum. The amount of metal particles is from about 0.001 to about 8 µg/cm² on the surface. A preferred amount of the metal particles is from about 0.01 to about 4 µg/cm². A particularly preferred amount of the metal particles is from about 0.01 to about 1 µg/cm².

Either the substrate itself is electron donating or there is applied a layer of an electron donating material on the substrate. In the case where the electron donating material is applied on the substrate it is applied in an amount of from about 0.05 to about 12 µg/cm².

An electron donating material does not necessarily have an electron-donating surface. An example is aluminium, which in air gets an oxide layer, which is not an electron-donating surface.

The electron donating material is any material with the ability to form an electron-donating surface, such as a conducting polymer or a metal. In the case of a metal it must be less noble than any of the metals in the group consisting of palladium, gold, ruthenium, rhodium, osmium, iridium, and platinum.

A preferred metal for use as an electron-donating surface is a metal chosen from silver, copper and zinc.

In one embodiment of the present invention the substrate is a polymeric substrate.

In one embodiment the substrate is chosen from latex, polymers comprising vinyl groups, silicone, polyvinylchloride, polypropylene, polyurethane, polyester, copolymerisates of ethylene vinyl acetate, polystyrene, polycarbonate, polyethylene, polyacrylate, polymethacrylate, acrylonitrile butadiene styrene, polyamide, and polyimide, or mixtures thereof.

In another embodiment of the present invention the substrate is chosen from a natural polymer, a degradable polymer, an edible polymer, a biodegradable polymer, an environmental friendly polymer, and a medical grade polymer.

In another embodiment of the present invention the substrate is a metal.

A preferred metal for the substrate is chosen from stainless steel, medical grade steel, titanium, medical grade titanium, cobalt, chromium and aluminium or mixtures thereof. In another embodiment of the present invention the substrate is chosen from glass, minerals, zeolites, stone and ceramics.

In another embodiment of the present invention the substrate is chosen from paper, wood, woven fibres, fibres, cellulose fibres, leather, carbon, carbon fibres, graphite, polytetrafluoroethylene, and polyparaphenyleneterephthalamide.

In another embodiment of the present invention the substrate has the shape of a particle. In this embodiment particles are coated according to the present invention. Such particles can have a spherical shape or an irregular shape.

In one embodiment of the present invention there is provided an object comprising a substrate according to the present invention. Examples of an object comprising a substrate according to the present invention are medical devices, medical instruments, disposable articles, medical disposable articles.

The particles must always include palladium. In addition to palladium there is at least one other metal. A ratio of palladium to other metals in the metal particles of from about 0.01:99.99 to about 99.99:0.01 can be used in the present invention. A ratio from about 0.5:99.5 to about 99.8:0.2 is preferred. Particularly preferred ratios are from about 2:98 to about 95:5. Very particularly preferred ratios are 5:95 to 95:5. In another embodiment the ratios are from about 10:90 to about 90:10.

In one embodiment of the present invention the metal particles, in addition to palladium, include gold.

The present inventors have discovered that advantageous properties are achieved when the metal particles have an average size of from about 10 to about 10000 Å.

In one embodiment the average sizes for said metal particles are from about 100 to about 600 Å.

In another aspect of the present invention there is provided an object including any of the substrates described herein.

There is also provided a medical device comprising any of the substrates described herein.

A disposable article comprising any of the substrates described herein is also provided.

The present invention also provides a dental article, as well as dental equipment, dental implants, and dental devices, comprising any of the substrates described herein.

The applied amount of the metal particles is expressed as a surface concentration in µg/cm² and it must be realised that the metal particles do not form a covering layer, but instead are uniformly distributed particles or clusters on said electron donating surface. Thus this is a measure of the weight of the particles on an area of the substrate.

An applied layer of an electron donating material is preferably applied so that it is uniform, essentially without agglomerates or clusters on the surface. If the electron donating surface layer is homogenous and uniform the applied amount in µg/cm² may be converted to a thickness in Å. An applied amount of 0.05-4 µg/cm² corresponds to about 4.8-380 Å, 0.5-8 µg/cm² corresponds to about 48-760 Å, and 0.8-12 µg/cm² corresponds to about 76-1140 Å.

In one embodiment of the present invention the electron-donating surface is a layer of commercially available essentially pure silver, which does not exclude the possibility of small amounts of impurities.

If the substrate does not have an electron donating surface and thus a deposition of an electron donating surface layer is necessary, the deposition is performed using a method chosen from chemical vapour deposition, sputtering, and deposition of metal from a solution comprising a metal salt. A uniform layer essentially without clusters or agglomerates is the result of the deposition. Preferably the deposition is carried out so that the first layer has good adhesion to the substrate.

Now there is described one embodiment of the present invention for preparation of the coated substrate. For substrates which do not have an electron donating surface the method includes some or all of the following steps:
1. pre-treatment
2. rinsing
3. activation
4. deposition of an electron donating surface
5. rinsing
6. deposition of metal particles
7. rinsing
8. drying For objects with an electron-donating surface the method comprises the steps
1. rinsing
2. deposition of metal particles
3. rinsing
4. drying In the following, one embodiment of steps 1 to 8 for substrates which do not have an electron-donating surface are described more in detail.

The pre-treatment can be made in an aqueous solution of a stannous salt containing from about 0.0005 to about 30 g/l of stannous ions. The pH is from about 1 to about 4 and adjusted by hydrochloric and/or sulphuric acid. The treatment time is from about 2 to about 60 minutes at room temperature. After the pre-treatment the surface is rinsed in demineralised water, but not dried.

The activated and rinsed substrate is transferred to the deposition solution. The deposition solution has a pH of not less than about 8. It includes a metal salt chosen from a silver salt, a zinc salt, and a copper salt. In one embodiment of the present invention the salt is silver nitrate ($AgNO_3$). The metal salt is used in an effective amount of no more than about 0.10 grams per litre, preferably about 0.015 grams per litre. If the metal content is above about 0.10 grams per litre, the elemental metal may form nonuniformly, in the solution or on the container walls. If the metal content is below an effective amount, there is insufficient metal to form a film in the desired time.

A second component of the deposition solution is a reduction agent that reduces the metal-containing salt to elemental metal. The reduction agent must be present in an amount sufficient to accomplish the chemical reduction. Acceptable reduction agents include formaldehyde, hydrazine sulphate, hydrazine hydroxide, and hypo phosphoric acid. In one embodiment of the present invention it is present in an amount of about 0.001 millilitres per litre of solution. Too large a concentration of the reduction agent causes deposition of metal throughout the solution and on the container walls, while too small a concentration may result in an insufficient formation of metal on the substrate. A person skilled in the art can in the light of this description by routine experimentation determine the desired amount of reduction agent.

Another component of the deposition solution is a deposition control agent that is present in an amount sufficient to slow the deposition reaction to prevent the reduced metal from precipitating directly from solution as a fine metallic powder, or precipitating onto the walls of the container. Operable deposition control agents include inverted sugar, also known as invertose, succinic acid, sodium citrate, sodium acetate, sodium hydroxide, potassium hydroxide, sodium tartrate, potassium tartrate, and ammonia. The deposition control agent is preferably present in an amount of about 0.05 grams per litre of solution. If too little is present, there may occur precipitation of metal clusters instead of a uniform metallic surface. If too much is present, the metal-containing salt may become too stable for the desired precipitation onto the substrate of interest.

The concentrations of the reduction agent and the deposition control agent are adjusted as necessary to achieve the desired results, depending upon the substrate material, the thickness of the film desired, the conditions of deposition, and the concentration of metal in the solution. For example, for thin films the metal salt concentration will be relatively low, as will the concentrations of the reduction agent and the deposition control agent. A person skilled in the art can in the light of this description by routine experimentation determine the desired amount of deposition control agent.

In preparing the deposition solution, each of the components of the solution are preferably individually dissolved in demineralised water. The various pre-solutions are then mixed, and diluted where necessary, in the correct amounts to achieve the concentrations mentioned above.

The combination of a metal salt and reduction agent permits the metal to be reduced from the salt in a suitable state to be deposited upon the surface of the substrate. This method is particularly beneficial to achieve good adhesion of the completed metal film to the substrate surface. Good adhesion is important in nearly all uses.

The substrate surface is exposed to the deposition solution by any appropriate procedure. Dipping into the solution is normally preferred, but the solution may be applied by any convenient technique such as spraying or brushing. The metal film deposits uniformly from the solution at a rate that may be controlled by the concentration of the metal salt. If a thin film is required, the temperature of deposition is maintained sufficiently low so that deposition is controllably slow.

Other methods of applying a metal layer that acts as an electron-donating surface can also be applied in the present invention. Other ways of achieving an electron-donating surface include chemical vapour deposition and sputtering.

After the above-described metal deposition the substrate has an electron-donating surface consisting of a metal. This metal deposition is only necessary if the substrate does not have an electron-donating surface from the start. If the substrate already possesses an electron-donating surface, metal particles can be deposited on the surface without the extra addition of a metal layer. In the latter case the substrate is cleaned thoroughly before application of the particles.

The next step in the manufacturing method is deposition of metal particles.

In one embodiment colloidal suspensions of metals are used to obtain particles comprising palladium and at least another metal on the surface. The metal particles are deposited from a suspension of the desired particles. The composition of the metal particles in the suspension is adjusted according to the preferred value. The substrate with the electron-donating surface is dipped in the suspension of metal particles for a period of time from about a few seconds to about a few minutes or longer.

The suspension of metal particles can be manufactured in several ways. In one embodiment the suspension of metal particles is made from an aqueous solution of a metal salt which is reduced under conditions such that metal particles of a desired size are formed. Mixing a suitable amount of metal salt, reducing agent and stabilising agent achieves this. The same reducing agents and stabilising agents as described above can be used when making the particle suspension. A person skilled in the art can in the light of this description by routine experimentation determine the desired amount of reducing agent and stabilising agent to get the desired particle size. In an alternative embodiment a commercially available colloidal suspension of metal particles is used. Metal particles of the desired composition are used to make the suspension.

In one embodiment the suspension of metal particles is made by diluting with demineralised water a commercially available concentrated colloidal solution of metal particles comprising palladium and at least one metal chosen from gold, ruthenium, rhodium, osmium, iridium, and platinum. The substrate is treated with the suspension for a period of time from about a few seconds to about a few minutes or longer. After the treatment the substrate is rinsed in a solvent or water such as demineralised water and left to dry in room temperature.

In one particular non-limiting embodiment the commercially available metal particles consist of 75% palladium and 25% gold.

Thus according to the present invention, a substrate with a particular desired surface can be obtained. For example, one can prepare a substrate having a silver electron donating surface with particles consisting of 75% palladium and 25% gold, or a copper electron donating surface with particles consisting of 85% palladium and 15% ruthenium.

One of the advantages offered by the flexible yet controlled and repeatable method for producing such substrates is that a wide variety of substrates can be produced. As described further herein, certain substrates have improved properties over existing substrates. For example a particular substrate according to the present invention can produce surprising and advantageous modifications of the hydrophobicity of a substrate to which is it applied. Other properties that can be modified in this way by substrates according to claim 1 include protein adsorption and adhesion of bacteria.

That is, it is possible to adjust the particle size, the composition of the particles and the amount of particles to modify the surface properties of objects to which the substrate is applied.

The present inventors have discovered that it is possible to achieve this by using a substrate according to claim 1. In particular it is possible to adjust the particle size, the composition of particles, and the amount of particles to modify the surface properties.

Substrates according to the present invention can be used for many purposes. They are suitable for use in any application where it is desired to modify hydrophobicity, protein adsorption, and adhesion of bacteria of a substrate.

Properties of the substrate can be both reduced or increased. Thus objects are provided which display at least one area which enhances a feature, and at least one area which reduces a feature. An example is an object with an area that reduces protein adsorption and an area that enhances protein adsorption.

A substrate according to the present invention also comprises a substrate having an electron donating surface, with metal particles on said surface, said metal particles comprise palladium wherein the amount of said metal particles is from about 0.001 to about 8 µg/cm².

The present invention provides use of a substrate according to the present invention for modifying the protein adsorption to an object comprising said substrate. An example of use is to adjust the protein adsorption onto a medical device to a desired level.

The present invention provides use of a substrate according to the present invention for modifying the bacterial adhesion to an object comprising said substrate.

The present invention provides use of a substrate according to the present invention for preventing bacterial growth.

The present invention provides use of a substrate according to the present invention for preventing colonisation of bacteria.

An example of this where it is important to modify the adhesion of bacteria, preventing bacterial growth and preventing colonisation of bacteria is a catheter to be inserted in a body, where the adhesion of bacteria, bacterial growth and colonisation of bacteria should be as low as possible.

The present invention provides use of a substrate according to the present invention for preventing transmission of bacteria. Transmission of bacterial infections is prevented by the prevention of the transmission of bacteria. Examples of objects used in this context are handles, buttons, switches, hospital equipment, surgical instruments, medical instruments, kitchen equipment, and all other objects, which are able to transmit bacteria.

The present invention provides use of a substrate according to the present invention for preventing transmission of a nosocomial infection. An object comprising a substrate according to the present invention can be used in any context where it is desired to prevent transmission of a bacterial infection. Preventing transmission of bacteria and thus bacterial infections will in particular prevent nosocomial infections.

Other features of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Hydrophobicity of the Surface as a Function of the Amount of Metal Particles

A uniform layer of silver was deposited on a glass substrate according to the following method. The substrate was immersed in a cleaning solution of chromic acid for 5 minutes at 58° C., followed by rinsing in demineralised water. The surface of the substrate was activated by immersion in a solution of aqueous stannous chloride and then rinsed in demineralised water. The surface of the substrate was then plated with a uniform layer of silver by immersion in 3 deposition solutions comprising silver ions. This yielded a silver surface with an applied amount of 1.2 µg/cm² corresponding to a thickness of about 115 Å. Particles consisting of 23% palladium and 77% gold were subsequently deposited on the first silver surface by immersion in a dilute suspension comprising metal particles of gold/palladium. The suspension of metal particles was made by reducing a gold salt and a palladium salt with a reducing agent and stabilising the suspension with a stabilising agent. The substrate was subsequently rinsed in demineralised water and dried.

Substrates with different amounts of deposited particles were made using the method outlined above. Amounts of particles were 0, 0.02, 0.11, 0.15, and 0.19 µg/cm² respectively. For the sample with 0 µg/cm² no particles were deposited on the surface and hence it consists of a silver surface.

The static contact angle of a drop of water in equilibrium on the different substrates was measured. The advancing and receding contact angles were measured using the Wilhelmy technique.

The difference between the advancing and receding contact angle values is called the contact angle hysteresis and was calculated for the measurements. The result of the experiment is depicted in Table 1.

TABLE 1

| Amount of particles (µg/cm²) | Static contact angle (degrees) | Contact angle hysteresis (degrees) |
| --- | --- | --- |
| 0 | 52 | 70 |
| 0.02 | 50 | 77 |
| 0.11 | 56 | 75 |
| 0.15 | 62 | 80 |
| 0.19 | 62 | 84 |

The surface hydrophobicity of the substrate is thus modified while the surface displays several other useful properties, such as antimicrobial properties, inherent of the substrates according to this example.

Example 2

Protein Adsorption as a Function of the Amount of Metal Particles

A uniform layer of silver was deposited on a silicon dioxide substrate. The substrate was immersed in a cleaning solution of 20% sulphuric acid for 10 minutes at room temperature, followed by rinsing in demineralised water. The surface of the substrate was activated by immersion in an aqueous solution of stannous chloride and the rinsed in demineralised water. The surface of the substrate was then plated with a uniform layer of silver by immersion in 4 baths of deposition solutions comprising silver ions. This yielded a silver surface with an applied amount of 0.8 µg/cm$^2$ corresponding to a thickness of about 77 Å. Particles consisting of 95% palladium and 5% gold were subsequently deposited on the first silver surface by immersion in a dilute suspension of Pd/Au-particles. The applied amount of metal particles was 0.05, 0.12, 0.48 and 0.59 µg/cm$^2$ respectively. The substrate was rinsed in demineralised water and dried.

Adsorption of fibrinogen was studied by the QCM-D technique. Fibrinogen is a glycoprotein synthesised in the liver and is found in blood plasma. QCM-D is a quartz crystal microbalance with dissipation monitoring.

The adsorbed amount of fibrinogen as a function of applied metal particles is shown in table 2.

TABLE 2

| Amount of Pd/Au-particles (µg/cm$^2$) | Fibrinogen adsorption (µg/cm$^2$) |
|---|---|
| 0.05 | 2.5 |
| 0.12 | 2.8 |
| 0.48 | 1.8 |
| 0.59 | 2.3 |

Example 3

Growth of Bacteria as a Function of the Amount of Metal Particles

Palladium/gold nanoparticles were deposited in different amounts on a silver base layer, following the method outlined in example 1. The particles comprised 95% palladium and 5% gold. The amount of silver in the base layer was kept constant for all samples. Hence the amount of deposited Pd/Au particles was varied. The growth of bacteria as a function of amount of deposited nanoparticles (Pd/Au) was studied using the following method:

Coated samples were placed into universals. Triplicates were included for each test condition 10 ml of artificial urine (AU) containing inoculated E. coli (roughly 10$^5$ CFU/ml) was added to each one and they were incubated horizontally with gentle shaking at 37° C. for 4 hours.

After 4 hours the universals were removed from incubation. The samples were removed and CFU (colony forming unit) counts were done from each universal by carrying out 10-fold dilutions in sterile distilled water and plating 100 µl onto a third of a nutrient agar plate. These were incubated for 16-24 hours at 37° C. and the colonies counted. The reduction in log CFU/ml versus a control was calculated and is shown in Table 3.

TABLE 3

| Amount of nanoparticles (Pd/Au) (µg/cm$^2$) | Reduction in Log CFU/ml read vs. control |
|---|---|
| 0.78 | 6.5 |
| 0.84 | 7.0 |
| 1.03 | 6.0 |
| 1.10 | 6.5 |
| 1.74 | 5.3 |
| 2.35 | 4.9 |
| 2.41 | 4.6 |

Example 4

Microbial Growth for Several Species

Palladium/gold nanoparticles were deposited in different amounts on a silver base layer on a substrate of silicone, following the method outlined in example 1. The particles comprised 95% palladium and 5% gold. The amount of silver in the base layer was kept constant for all samples. The amount of deposited Pd/Au particles was 0.36 µg/cm$^2$. The antimicrobial properties for different bacterial strains were studied.

Species of microorganisms were chosen with the goal to survey a range of common pathogens (clinical isolates) involved in bacteria transmission and nosocomial infections, namely *Escherichia coli* (*E. coli*), *Pseudomonas aeruginosa* (*P. aeruginosa*), *Enterococcus* spp, *Klebsiella*, and *Candida*.

The Pd/Au coated silicone samples were placed into universals. Triplicates were included for each test condition. 10 ml of artificial urine containing inoculated organisms (roughly 10$^5$ CFU/ml) was added to each one and they were incubated horizontally with gentle shaking at 37° C. for 24 hours.

After 24 hours the universals were removed from incubation. The samples were removed, drained on paper towels and then placed into universals containing 20 ml PBS+Tween and sonicated for 1.5 minutes.

CFU counts were done from each universal by carrying out 10-fold dilutions in sterile distilled water and plating 100 µl onto a third of a nutrient agar plate. These were incubated for 16-24 hours at 37° C. and the colonies counted. In table 4 the reduction of bacteria compared to the uncoated silicone sample is shown. The larger the value the greater reduction.

TABLE 4

| | Reduction vs. Control (Log CFU/cm) | | | | |
|---|---|---|---|---|---|
| | E. coli | P. aeruginosa | Enterococcus | Klebsiella | Candida |
| Uncoated silicone | 0.00 | 0.00 | 0.00 | 0.00 | 0.00 |
| Pd/Au particle coated silicone | 1.64 | 2.53 | 3.88 | 1.37 | 2.52 |

Example 5

Primary Adhesion and Cell Recovery of *P. Aeruginosa*

Palladium/gold nanoparticles were deposited in different amounts on a silver base layer, following the method outlined in example 1. The amount of silver in the base layer was kept constant for all samples. The amount of Au and Pd in the particles was varied according to table 5.

The samples were challenged with radiolabled *P. aeruginosa* GSU-3, and allowed to incubate for a period of two hours.

Primary attached cells on the samples and cell recovery was determined (ability for the cells to recover). The method employed in this study was the one described in M. M. Gabriel et al., Current Microbiology, vol. 30 (1995), pp. 17-22, mutatis mutandis. The results are summarized in Table 5 below.

TABLE 5

| Sample No | Amount Au ($\mu g/cm^2$) | Amount Pd ($\mu g/cm^2$) | Primary Adhesion $CFU/mm^2$ | Cell recovery Percent Reduction |
|---|---|---|---|---|
| 1 | 0.08 | 1.17 | $2.45*10^4$ | 93 |
| 2 | 0.31 | 0.95 | $2.8*10^4$ | 95.3 |
| 3 | 1.01 | 0.56 | $3.2*10^4$ | 89.9 |
| 4 | 1.1 | 0.26 | $3.45*10^4$ | 93 |
| 5 | 0.98 | 0.02 | $3.4*10^4$ | 94.4 |
| Silicone Control (uncoated) | 0 | 0 | $4.85*10^4$ | 0 |

Example 6

A net of polyester fabric was first rinsed in a 5% potassium hydroxide solution for 5 min at 30° C. After repeated rinsing in demineralised water the substrate was immersed in an acidified solution of 1 g/l stannous chloride at room temperature for 10 min. After rinsing in demineralised water it was soaked in a plating bath containing 2 g/l copper sulphate, 5 g/l sodium hydroxide, 50 g/l sodium citrate and 0.005 ml/l formaldehyde for 10 min at 35° C. A copper layer of about 200 Å was obtained and after new rinsing in demineralised water the substrate was immersed in a particle suspension comprising 0.05 g/l each of palladium particles and gold particles. The applied amount of metal particles was 0.4 $\mu g/cm^2$.

Example 7

A substrate of PMMA was cleaned in 5% hydrochloric acid for 2 min and then rinsed in demineralised water before dipping in a solution containing 0.02 g/l of the stannous ion at a pH of 2.5. After rinsing the substrate was immersed in a solution containing 0.005 g/l of silver ions, 0.02 ml/l ammonia, 0.05 g/l potassium hydroxide and 0.0005 ml/l formaldehyde for 5 min at room temperature. This gave a surface with 0.12 $\mu g/cm^2$ of silver. After rinsing it was immersed in a particle suspension comprising 0.005 g/l palladium and 0.002 g/l gold particles. The applied amount of metal particles was 0.05 $\mu g/cm^2$.

Example 8

A non-woven polyimide substrate was immersed in a 12% solution of NaOH at 40° C. for 10 min. After repeated rinsing in demineralised water it was immersed in an alcoholic solution containing 0.5 g/l stannous chloride for 5 min at room temperature. After rinsing it was soaked in a copper bath according to example 3. A copper layer of 2 $\mu g/cm^2$ was obtained. After rinsing it was immersed in a suspension comprising 1% of Pd and 0.2% of gold particles, calculated on the weight of the total suspension. The applied amount of metal particles was 0.6 $\mu g/cm^2$.

Example 9

A nylon fabric was cleaned in 5% NaOH for 10 min at 40° C. and after rinsing in demineralised water immersed in a solution of 0.6 g/l stannous chloride at pH 2.2 for 15 min at room temperature. After this the surface comprised a silver amount of 0.8 $\mu g/cm^2$. After a new rinsing it was dipped in a silver bath according to example 2 and then after new rinsing dipped in a suspension comprising 1% Pd and 0.05% Au particles. The applied amount of metal particles was 0.12 $\mu g/cm^2$.

Example 10

A substrate of aluminium was treated in a solution of 10% nitric acid and 3% hydrofluoric acid at 60° C. for 20 min. After rinsing, the substrate was dipped in an acidified solution of 3 g/l stannous chloride and after renewed rinsing in a silver bath according to example 2. After this step an amount of around 80 Å silver was obtained on the surface. After another rinsing the substrate was immersed in a suspension comprising 1% Pd and 2% Au particles. The applied amount of metal particles was 0.7 $\mu g/cm^2$.

Example 11

A substrate of PTFE was etched in an aqueous solution of sodium hydroxide for 5 min. After rinsing and drying it was immersed in a solution containing 0.7 g/l stannous chloride for 20 min at room temperature. The substrate was after rinsing dipped in a plating bath containing 0.2 g/l silver nitrate, 0.5 ml/l ammonia and sodium hydroxide to pH 10.5 for 5 min. After this step an amount of around 2.2 $\mu g/cm$ silver was obtained on the surface. After a new rinse it was immersed in a suspension comprising 3% Pd and 0.1% Au particles for 5 min at room temperature. The applied amount of metal particles was 0.03 $\mu g/cm^2$.

Example 12

A glass plate was rinsed in 10% sulphuric acid and 1% hydrofluoric acid at room temperature for 15 min. After rinsing it was immersed in a 1% stannous fluoride solution and after a new rinse immersed in a silver bath according to example 2. After this step an amount of around 140 Å silver was obtained on the surface. After renewed rinsing it was dipped in a suspension comprising 1% ruthenium and 2% palladium particles. The applied amount of metal particles was 0.25 $\mu g/cm^2$.

Example 13

A stainless steel substrate was immersed in a solution of 15% nitric acid and 5% HF at room temperature for 30 min and then rinsed in demineralised water. The process continued following the steps in example 11. The applied amount of metal particles was 0.9 $\mu g/cm^2$.

Example 14

A titanium rod was cleaned in a solution of 18% nitric acid and 2% HF for 20 min at room temperature. The application of an electron donating surface and the application of metal particles was made as in example 11. The applied amount of metal particles was 0.6 μg/cm².

The invention claimed is:

1. A method of reducing or preventing bacterial growth on a substrate, wherein the method comprises the following steps:
   a. providing a substrate base, wherein said substrate base comprises an electron donating surface; and
   b. depositing metal particles from a suspension of metal particles, at an amount of about 0.001 to about 8 μg/cm² on said surface;
   wherein said metal particles comprise palladium and at least one non-palladium metal selected from the group consisting of gold, ruthenium, rhodium, osmium, iridium, and platinum,
   wherein said metal particles have an average size of about 100 to about 10,000 Å, wherein said particles are distributed particles or clusters on said surface, and
   wherein the metal particles do not form a covering layer.

2. The method according to claim 1, wherein said electron donating surface is a layer of an electron donating material in an amount of about 0.05 to about 12 μg/cm².

3. The method according to claim 1, wherein said layer of an electron donating material is a metal that is less noble than palladium, gold, ruthenium, rhodium, osmium, iridium, and platinum.

4. The method according claim 1, wherein said layer of an electron donating material is a metal selected from the group consisting of silver, copper, and zinc.

5. The method according claim 1, wherein said substrate base is a polymeric substrate base.

6. The method according claim 1, wherein said substrate is selected from the group consisting of latex, polymers comprising vinyl groups, silicone, polyvinylchloride, polypropylene, polyurethane, polyester, polystyrene, polycarbonate, polyethylene, polyacrylate, polymethacrylate, acrylonitrile butadiene styrene, polyamide, and polyimide, or mixtures thereof.

7. The method according claim 1, wherein said substrate is selected from the group consisting of a natural polymer, a degradable polymer, an edible polymer, a biodegradable polymer, and a medical grade polymer.

8. The method according claim 1, wherein said substrate is a metal.

9. The method according claim 1, wherein said substrate is selected from the group consisting of stainless steel, titanium, cobalt, and chromium or mixtures thereof.

10. The method according claim 1, wherein said substrate is selected from the group consisting of glass, minerals, zeolites, stone and ceramics.

11. The method according claim 1, wherein said substrate is selected from the group consisting of paper, wood, woven fibres, fibres, cellulose fibres, leather, carbon, carbon fibres, graphite, polytetrafluoroethylene, and polyparaphenyleneterephthalamide.

12. The method according claim 1, wherein the amount of the metal particles on the electron donating surface is from about 0.01 to about 4 μg/cm².

13. The method according claim 1, wherein the weight ratio of palladium to the at least one metal selected from the group consisting of gold, ruthenium, rhodium, osmium, iridium, and platinum in said metal particles is from about 0.01:99.99 to about 99.99:0.01.

14. The method according claim 1, wherein the weight ratio of palladium to the at least one metal selected from the group consisting of gold, ruthenium, rhodium, osmium, iridium, and platinum in said metal particles is from about 0.5:99.5 to about 99.8:0.2.

15. The method according claim 1, wherein the weight ratio of palladium to the at least one metal selected from the group consisting of gold, ruthenium, rhodium, osmium, iridium, and platinum in said metal particles is from about 2:98 to about 95:5.

16. The method according claim 1, wherein the at least one metal is gold.

17. The method according claim 1, wherein said metal particles on the electron donating surface have average sizes of about 100 to about 600 Å.

18. The method according to claim 1, further comprising the step of:
   bringing the substrate having deposited metal particles into contact with bacteria.

* * * * *